United States Patent
Hieftje et al.

(10) Patent No.: US 9,607,306 B2
(45) Date of Patent: Mar. 28, 2017

(54) AMBIENT SAMPLING MASS SPECTROMETRY AND CHEMOMETRIC ANALYSIS FOR SCREENING ENCAPSULATED ELECTRONIC AND ELECTRICAL COMPONENTS FOR COUNTERFEITS

(71) Applicants: Indiana University Research & Technology Corporation, Indianapolis, IN (US); United States of America as represented by the Secretary of the Navy, Washington, DC (US)

(72) Inventors: Gary M. Hieftje, Bloomington, IN (US); Steven J. Ray, Bloomington, IN (US); Kevin P. Pfeuffer, Bloomington, IN (US); Jacob T. Shelley, Stow, OH (US); Norris J. Caldwell, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/662,109

(22) Filed: Mar. 18, 2015

(65) Prior Publication Data

US 2015/0269592 A1 Sep. 24, 2015

Related U.S. Application Data

(60) Provisional application No. 61/955,296, filed on Mar. 19, 2014.

(51) Int. Cl.
*H01J 49/00* (2006.01)
*G06Q 30/00* (2012.01)
*G06F 19/00* (2011.01)
*H01J 49/14* (2006.01)

(52) U.S. Cl.
CPC ......... *G06Q 30/0185* (2013.01); *G06F 19/70* (2013.01); *H01J 49/142* (2013.01)

(58) Field of Classification Search
USPC .......................... 361/751; 250/288, 389, 281
See application file for complete search history.

(56) References Cited

U.S. PATENT DOCUMENTS

| | | | | |
|---|---|---|---|---|
| 6,060,169 A | * | 5/2000 | Kuczynski | G06K 19/073 361/751 |
| 2008/0067352 A1 | * | 3/2008 | Wang | H01J 49/0463 250/288 |

(Continued)

OTHER PUBLICATIONS

M. Pecht and S. Tiku, IEEE Spectrum, 2006, 43, 37-46.

(Continued)

*Primary Examiner* — Daniel Hess
(74) *Attorney, Agent, or Firm* — Barnes & Thornburg LLP

(57) ABSTRACT

A method and apparatus for identification of a counterfeit electronic component, subjecting a suspected counterfeit electronic to an analytical method of ambient surface analysis to desorb and ionize compounds directly from a suspected counterfeit electronic surface with no pretreatment, detecting the resultant ions, comparing the identified ions to known standards, and returning a confidence that the suspected counterfeit electronic being analyzed is counterfeit.

19 Claims, 9 Drawing Sheets

(56) References Cited

U.S. PATENT DOCUMENTS

| | | | |
|---|---|---|---|
| 2009/0001262 A1* | 1/2009 | Visser | H01J 49/0036 250/282 |
| 2015/0069254 A1* | 3/2015 | Fernandez | G01N 27/622 250/389 |
| 2015/0078518 A1* | 3/2015 | Tziazas | G06T 7/001 378/53 |

OTHER PUBLICATIONS

W. W. A. J. Ukman, in Chinese counterfeit parts found in U. S. weapons, Washington Post, Katharine Weymouth, Washington D.C., 2011.

J. Pelofsky, in Fake chips from China sold to U.S. defense contractors, Reuters, Tomson Reuters, Washington D.C., 2010.

P. J. Toren, in the Serious Risks From Counterfeit Electronic Parts, Forbes, New York City, 2012, http://Forbes. com.

D. Lin, in Counterfeit Chips Plague U.S. Missile Defense, Conde Nast Publishing, New York City, 2011, http://Wired.com.

B. Sood, D. Das and M. Pecht, J. Mater. Sci.: Mater. Electron., 2011, 22, 1511-1522.

Z. Takats, J. M. Wiseman, B. Gologan and R. G. Cooks, Science, 2004, 306, 471-473.

A. B. Costa and R. Graham Cooks, Chem. Phys. Lett., 2008, 464, 1-8.

R. B. Cody, J. A. Laramee and H. D. Durst, Anal. Chem., 2005, 77, 2297-2302.

J. D. Harper, N. A. Charipar, C. C. Mulligan, X. Zhang, R. G. Cooks and Z. Ouyang, Anal. Chem., 2008, 80, 9097-9104.

J. T. Shelley and G. M. Hieftje, J. Anal. At. Spectrom., 2010, 25, 345-350.

J. T. Shelley, J. S. Wiley and G. M. Hieftje, Anal. Chem., 2011, 83, 5741-5748.

C. Zhen, Y. Zhou, N. Zhang, J. Wang, C. Xiong, S. Chen and Z. Nie, Analyst, 2013, 138, 3830-3835.

T. Cajka, K. Riddellova, M. Tomaniova and J. Hajslova, Metabolomics, 2011, 7, 500-508.

F. M. Fernandez, R. B. Cody, M. D. Green, C. Y. Hampton, R. McGready, S. Sengaloundeth, N. J. White and P. N. Newton, ChemMedChem, 2006, 1, 702-705.

L. Nyadong, M. D. Green, D. Jesus, V. R., P. N. Newton and F. M. Fern'andez, Anal. Chem., 2007, 79, 2150-2157.

G. A. Harris, L. Nyadong and F. M. Fernandez, Analyst, 2008, 133, 1297-1301.

M. C. Jecklin, G. Gamez and R. Zenobi, Analyst, 2009, 134, 1629-1636.

R. A. Lodder, M. Selby and G. M. Hieftje, Anal. Chem., 1987, 59, 1921-1930.

R. A. Lodder and G. M. Hieftje, Appl. Spectrosc., 1988, 42, 1351-1365.

R. A. Lodder and G. M. Hieftje, Appl. Spectrosc., 1988, 42, 1500-1512.

R. A. Lodder and G. M. Hieftje, Appl. Spectrosc., 1988, 42, 309-312.

Y. Zou, Y. Xia, A. R. Jones and R. A. Lodder, Anal. Chem., 1993, 65, 434A-439A.

R. J. Dempsey, D. G. Davis, R. G. Buice and R. A. Lodder, Appl. Spectrosc., 1996, 50, 18A-34A.

J. T. Shelley and G. M. Hieftje, Analyst, 2010, 135, 682-687.

K. P. Pfeuffer, J. T. Shelley, S. J. Ray and G. M. Hieftje, J. Anal. At. Spectrom., 2013, 28, 379-387.

K. Pfeuffer, S. Ray and G. Hieftje, J. Am. Soc. Mass Spectrom., 2014, 25, 800-808.

H. L. Mark and D. Tunnell, Anal. Chem., 1985, 57, 1449-1456.

* cited by examiner

AMBIENT SAMPLING MASS SPECTROMETRY AND CHEMOMETRIC ANALYSIS FOR SCREENING ENCAPSULATED ELECTRONIC AND ELECTRICAL COMPONENTS FOR COUNTERFEITS

CROSS-REFERENCE TO RELATED APPLICATIONS

This application claims the benefit under 35 U.S.C. §119 (e) of the Mar. 19, 2014 filing date of U.S. Ser. No. 61/955,296. U.S. Ser. No. 61/955,296 is hereby incorporated herein by reference in its entirety.

BACKGROUND

Counterfeit electronics have recently been discovered to be an insidious problem within the supply chain for commercial and military applications. See, for example, Pelofsky, J., in *Reuters*. Thomson Reuters: Washington D.C., Tuesday, Oct. 26, 2010 edn., 2010, and Ukman, W. W. a. J., in *Washington Post*. Katharine Weymouth: Washington D.C., 2011. Illicit electronic components have been discovered in the inventories of several distributors and even installed in commercial and military products. Tracking components and tracing the validity of their origins are complicated by the diffuse nature of the supply chain, with its multiple distributors and manufacturers. The problem is compounded by the long times in service for military systems and, by comparison, the relatively short service lives of consumer electronic components. In particular, requirements to maintain and repair military systems create a need for integrated circuits (ICs) at times well after the manufacturing period of the original parts: such situations are ripe for counterfeiting.

Illicit or counterfeit electronic components include a broad category of devices that can range from the correct unit with a more recent date code to lower-specification or non-working systems with altered names, manufacturers and date codes. The term "counterfeit electronics" primarily refers to devices that have been mislabeled or relabeled to suggest higher manufacturing specifications (i.e. military spec) or newer manufacture dates. These chips typically will pass basic functionality tests, as they are often the correct type of device, but are outdated or of lower specification. One example of counterfeit electronic components is integrated circuits (ICs) that have been relabeled.

One relabeling technique is known as "blacktopping". The blacktopping process begins with removal of the original IC surface, along with the original lettering, typically by abrasive means. Then, a new surface (called 'blacktop' in view of its typical coloration) is applied to the IC, and fraudulent re-lettering with updated specifications, date (of manufacture) codes, etc., is applied, by a method such as ink printing or laser etching.

Current methodologies to detect counterfeits include visual inspection with microscopy by expert users and solvent testing for residues. These techniques, while effective, are time-consuming and rely on a skilled operator to both perform and interpret the results. More advanced microscopy techniques, such as scanning electron microscopy and scanning acoustic microscopy, are utilized along with X-ray techniques, such as imaging X-ray techniques to detect die shape and size irregularities and fluorescence X-ray techniques to detect usage of non-qualified materials (metals) in lead-solder coatings (e.g., for "tinning" of leads). These advanced techniques provide detailed information about potentially counterfeit chips. However, the instrumentation for these techniques is very expensive (>$100K), requires highly skilled operators, and is very slow, taking, for example, more than 5 minutes per test to interpret results for each chip.

Thus, there is a need within the supply chain itself and extending into the consumer-parts community for rapid but reliable screening techniques to detect the presence of blacktopped components; i.e., for analytical methodologies that can make sampling and analysis of the component surfaces more nearly "real time."

SUMMARY

According to an aspect of the invention, a method for identification of a counterfeit electronic comprises subjecting a suspected counterfeit electronic to an energy source to energize compounds at a surface of the suspected counterfeit electronic, detecting properties of the compounds at the surface, and comparing the properties of the compounds at the surface to a standard.

Illustratively, the energy source desorbs and ionizes the compounds at the surface of the suspected counterfeit electronic.

Illustratively, detecting properties of the compounds at the surface comprises generating a mass spectrum of ions resulting from the compounds at the surface.

Illustratively, the energy source is an ambient desorption/ionization (ADI) source.

Illustratively, the energy source is flowing atmospheric pressure afterglow (FAPA).

Illustratively, the energy source is Direct Analysis in Real Time (DART).

Illustratively, the energy source is selected from the group consisting of ultraviolet light, visible light, near-infrared light, infrared light.

Illustratively, the energy source is infrared or near-infrared light and the detecting properties step comprises correlation analysis.

Illustratively, the energy source is ultraviolet, visible, or near-infrared light and the detecting properties step comprises Raman scattering and spectral interpretation.

Illustratively, comparing the properties of the compounds at the surface to a standard comprises using a chemometric method to process data describing the properties of the compounds at the surface.

Illustratively, the chemometric method is a multivariate statistical technique.

Illustratively, the multivariate statistical technique is principal component analysis (PCA).

Illustratively, comparing the properties of the compounds at the surface to a standard further comprises using the bootstrapped error-adjusted single sample technique (BEAST).

Illustratively, the chemometric method is the bootstrapped error-adjusted single sample technique (BEAST).

Illustratively, detecting properties of the compounds at the surface comprises generating a mass spectrum of ions resulting from the compounds at the surface and the data comprise mass spectra.

Illustratively, the suspected counterfeit electronic is a suspected counterfeit integrated circuit and the standard is derived from a genuine integrated circuit.

Illustratively, the suspected counterfeit electronic is not pretreated.

Illustratively, the suspected counterfeit electronic is suspected of being altered by blacktopping.

According to another aspect of the invention, a method for identification of a counterfeit electronic comprises subjecting a suspected counterfeit integrated circuit to an ambient desorption/ionization (ADI) source to ionize and desorb compounds at a surface of the suspected counterfeit electronic, generating a mass spectrum of ions resulting from the compounds at the surface, and comparing the mass spectrum to a standard using a chemometric method.

Illustratively, the chemometric method is selected from the group consisting of principal component analysis (PCA), the bootstrapped error-adjusted single sample technique (BEAST), and a combination thereof.

According to another aspect of the invention, an apparatus for identification of a counterfeit electronic comprises an ambient desorption/ionization (ADI) source to desorb and ionize compounds directly from a surface of a suspected counterfeit electronic with no pretreatment, a mass spectrometry detector coupled to the ADI source to detect ions resulting from the surface, and at least one programmable machine programmed for comparing the ions to a standard by a chemometric method and returning a confidence that the suspected counterfeit electronic being analyzed is counterfeit.

Illustratively, the chemometric method is selected from the group consisting of principal component analysis (PCA) and the bootstrapped error-adjusted single sample technique (BEAST).

BRIEF DESCRIPTION OF THE DRAWINGS

The invention may best be understood by referring to the following detailed description and accompanying drawings which illustrate the invention. In the drawings.

DETAILED DESCRIPTIONS OF ILLUSTRATIVE EMBODIMENTS

Figure 1:
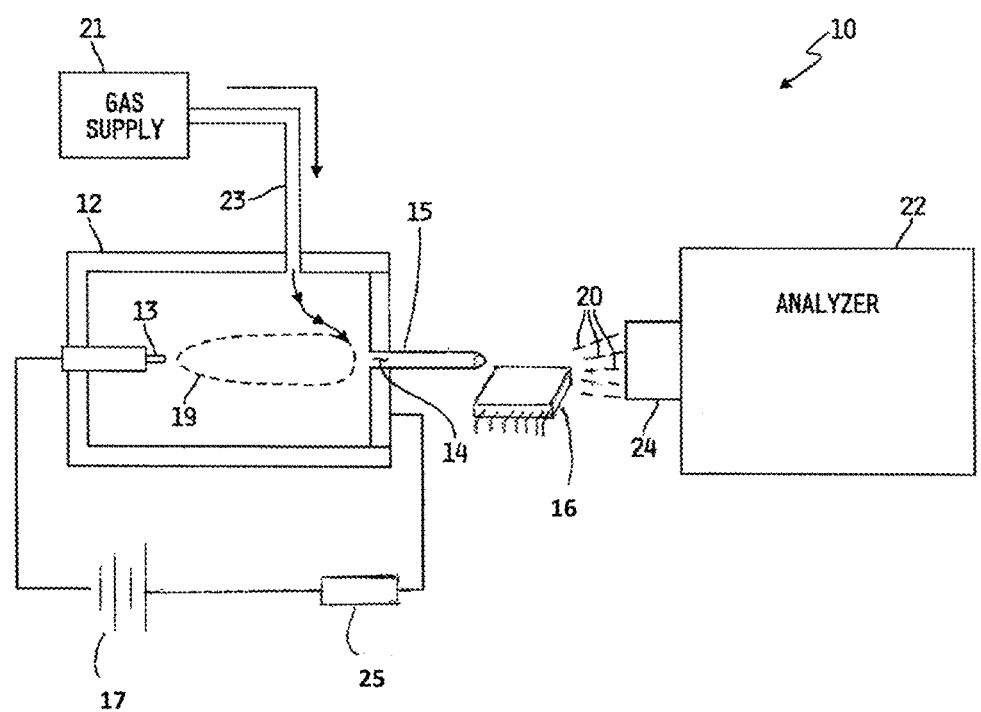
FIG. 1 is a schematic diagram of a pin-to-capillary FAPA source used for examination of integrated circuit (IC) surfaces for ambient mass spectrometry.

While the concepts of the present disclosure are susceptible to various modifications and alternative forms, specific illustrative embodiments and methods thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

References in the specification to "one embodiment", "an embodiment", "an illustrative embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

The illustrative embodiments described herein include a method for identification of a counterfeit electronic, such as an integrated circuit (IC). The method includes subjecting a suspected counterfeit electronic to an energy source to energize compounds at a surface of the suspected counterfeit electronic. In some embodiments, the energy source is capable of desorbing and ionizing the compounds at the surface of the suspected counterfeit electronic. In other embodiments, the energy source is ultraviolet, visible, near-infrared, or infrared light. The method further includes detecting properties of the compounds at the surface. In some embodiments, the methods described herein do not require pretreatment of the suspected counterfeit electronic. In some embodiments, the properties of the compounds at the surface are detected by generating a mass spectrum of ions resulting from the compounds at the surface after desorbing and ionizing the compounds. In other embodiments, the properties of the compounds at the surface are detected by near-infrared correlation spectroscopy, or by infrared or Raman spectroscopy. In embodiments that include near-infrared correlation spectroscopy, detecting properties includes correlation analysis. In embodiments that include infrared or Raman spectroscopy, detecting properties may include spectral interpretation. The method further includes comparing the properties of the compounds at the surface to a known standard. In some embodiments, the known standard is mass spectral data obtained from a genuine (non-counterfeit) electronic, which in some embodiments is an encapsulant standard. In other embodiments, the known standard is near-infrared correlation spectral data obtained from a genuine electronic. In yet other embodiments, the known standard is Raman or infrared spectral data obtained from a genuine electronic. It is to be appreciated that the properties of the known standard may be determined and recorded for use in comparing to other data at a later time or may be determined alongside detecting properties of the compounds at the surface of the suspected counterfeit electronic. In some embodiments, the comparing step includes using a chemometric method to process data, such as mass spectral data, near-infrared correlation spectral data, Raman-scattering data or infrared spectral data, for comparison to the known standard, which is mass spectral data, near-infrared correlation spectral data, Raman-scattering data or infrared spectral data. After the comparing step, a confidence may be provided to indicate how strongly the results of the comparing step indicate that an IC is genuine or counterfeit for each chip analyzed. The confidence limit can be controlled on the basis of the statistics software to tune the desired degree of sensitivity and accuracy.

As used herein, detecting properties of compounds at a surface of a suspected counterfeit electronic refers to determining properties such as chemical properties, physical properties, and spatial patterns related to such properties. The present disclosure contemplates, but is not limited to, for example, properties of compounds that are detectable by spectroscopic methods.

As used herein, the term "standard" refers to one or more values or properties that may be compared to properties of compounds at a surface of a suspected counterfeit electronic. In some embodiments, a "standard" may be a set of mass spectral data or other spectral data, processed or unprocessed by statistical techniques described herein.

As used herein, the term "chemometric method" refers to a mathematical or statistical method that may be applied to chemical data such as properties of one or more chemical compounds that have been detected as described herein.

As used herein, the term "pretreated" refers to a state of being prepared for use in an analytical instrument or method such that a sample is substantially not in its native state during analysis. For example, placing an IC in an apparatus described herein, such as the apparatus of FIG. 1, does not constitute pretreatment, but dissolving a sample in a solvent or chemically modifying the surface of an IC constitutes pretreatment.

The methods described herein include a method for determination, also referred to as identification, of electronics counterfeited by methods that involve changes in the surface of the target chip, such as by blacktopping, through use of ambient desorption/ionization mass spectrometry (ADI-MS), such as flowing atmospheric pressure afterglow (FAPA) ambient mass-spectrometry, near-infrared correlation spectroscopy, infrared or Raman spectroscopy, or other methods. The methods are coupled with chemometric methods. Ambient mass spectrometry permits generation of ions from samples in their native environment, and with no pretreatment. Elimination of sample pretreatment permits very rapid analysis, for example, less than 10 seconds per trial, of samples while retaining the sensitivity and specificity of mass spectrometry. The FAPA source utilizes an atmospheric-pressure glow-discharge (APGD) to desorb and ionize compounds directly from sample surfaces. The surface of a suspected chip is exposed to the effluent from the FAPA source and a fingerprint mass spectrum is generated in under 30 seconds. In some embodiments, an IC is subjected to an ADI-MS method and a confidence of whether the IC is counterfeit is returned in under about 60 seconds.

As used herein, the term "blacktopping" refers to a relabeling technique including modifying the surface of an integrated circuit or other labeled electronic to change its appearance. The blacktopping process generally begins with removal, typically by abrasive means, of the original IC surface that may contain for example the date code and part number of the IC. Then, a new surface, coating, print, or label (called "blacktop" in view of its typical coloration) is applied to the IC, and fraudulent re-lettering that may indicate updated specifications, date (of manufacture) codes, etc., is applied. Illustratively, the re-lettering may be accomplished by ink printing or laser etching. The re-surfacing itself could utilize any number of coating materials, ranging from matte-black inking or paint to appropriately particle-filled epoxy or urethane coatings. It is to be understood that a method of labelling a surface of an integrated surface that leads to an altered surface chemistry detectable by use of the analytical methods (for example, mass spectrometry, near IR correlation spectroscopy, IR spectroscopy and Raman spectroscopy) and chemometric methods (for example, principal component analysis of the bootstrapped error-adjusted single-sample technique) described herein constitutes "blacktopping."

As used herein, the term "ambient desorption/ionization mass spectrometry (ADI-MS)" refers to methods in which ions are created from the surface of a sample and directed into a mass spectrometer for chemical analysis. An example of ADI-MS includes Desorption ElectroSpray Ionization (DESI), as described by Z. Takats, J. M. Wiseman, B. Gologan and R. G. Cooks, Science, 2004, 306, 471-473; incorporated by reference herein in its entirety; which is able to generate a mass spectrum directly from a sample with little or no pretreatment by utilizing a stream of charged solvent droplets to solubilize, desorb and ionize samples from a surface and relies primarily on solvent extraction and partition for sampling. Another example of ADI-MS includes a plasma-based source, Direct Analysis in Real Time (DART), as described herein and as described in R. B. Cody, J. A. Laramée and H. D. Durst, Anal. Chem., 2005, 77, 2297-2302; incorporated by reference herein in its entirety; which utilizes a heated stream of helium from a corona discharge to thermally desorb and ionize compounds from a surface. Another example of ADI-MS includes a Low-Temperature Plasma probe (LTP), as described in J. D. Harper, N. A. Charipar, C. C. Mulligan, X. Zhang, R. G. Cooks and Z. Ouyang, Anal. Chem., 2008, 80, 9097-9104; incorporated by reference herein in its entirety. Another example of ADI-MS includes Flowing Atmospheric-Pressure (helium plasma) Afterglow (FAPA) as described herein and as described in J. T. Shelley and G. M. Hieftje, J. Anal. At. Spectrom., 2010, 25, 345-350 and J. T. Shelley, J. S. Wiley and G. M. Hieftje, Anal. Chem., 2011, 83, 5741-5748; both of which are incorporated by reference herein in their entirety. Several other sources for ADI-MS are known in the art, including but not limited to those described in G. A. Harris, L. Nyadong and F. M. Fernandez, Analyst, 2008, 133, 1297-1301; incorporated by reference herein in its entirety. Conceivably, any ADI-MS source could be used with the methods and system disclosed herein.

Referring to FIG. 1, a diagrammatic view of an embodiment of a system 10 configured for analyzing an integrated circuit 16 is shown. It is contemplated that the system 10 may also be used to analyze other electronics. The system 10 includes a glow discharge (GD) cell 12 having an orifice 14 directed towards the integrated circuit 16. In one embodiment, the GD cell 12 is operated at atmospheric pressure. As will be further described in detail herein, the GD cell 12 is configured to provide a flowing afterglow to the integrated circuit 16, which, through ionization and desorption, provides ionized particles 20 of the integrated circuit 16 for analysis by an analyzer 22. The ionized particles 20 may include molecules, molecular fragments, atoms, ions, etc. of the integrated circuit 16. FIG. 1 shows a diagrammatic internal view of the GD cell 12, which includes an electrode pin 13, also referred to as a pin cathode, and a FAPA exit capillary 15, also referred to as a capillary anode. In some embodiments, a power supply 17 coupled to a resistor 25 energizes the electrode pin 13 and the FAPA exit capillary 15, such that the electrode pin 13 serves as a cathode and the FAPA exit capillary 15 serves as an anode, so as to create an electrical glow discharge 19 in the GD cell 12. In some embodiments, the power supply 17 is a direct-current high-voltage power supply. Illustratively, the power supply 17 may be operated at about 400 V to about 500V, and the resistor may be a 5 kΩ resistor. The power supply 17 may be operated in various modes for various embodiments, such as current-controlled mode or voltage-controlled mode. Furthermore, it should be appreciated that the polarity of the power supply 17 shown in FIG. 1 may be reversed, such that the electrode pin 13 serves as an anode and the FAPA exit capillary 15 serves as a cathode. It should also be appreciated that one or more additional power supplies may be coupled to the system 10 at, for example, the FAPA exit capillary 15. It should also be appreciated that the power supply 17 could operate with alternating polarity.

A gas supply 21, which in one embodiment may be a helium supply, supplies gas through a supply line 23 into the GD cell 12, as indicated by the arrows. In one embodiment, high-purity helium (Ultra-high purity helium, Airgas Mid America, Bowling Green, Ky., for example) may be used. In one embodiment, the helium gas flow was set and monitored by a mass flow controller.

The glow discharge 19 is typically sustained in helium, including other trace impurity atmospheric gases, such that it produces effluents such as ions and excited species, which exit the GD cell 12 through the capillary 15 and interact with the atmosphere to generate reagent ions, typically protonated water clusters, which make up a flowing afterglow. The effluents flow to the integrated circuit 16 for ionization and desorption of compounds from the surface thereof. The integrated circuit is placed just below the inlet 24 such that ionized particles 20, which may include atoms, molecules, molecular fragments, etc., enter an inlet 24 of the analyzer 22 for analysis. It should be appreciated that various analyzers 22 may be used such as a time-of-flight mass spectrometer or an ion mobility spectrometer, for example.

It is to be understood that while the presented examples utilized a FAPA source as a means to desorb and ionize molecules from the suspected counterfeit electronics, this technique and these methods can be expanded to other plasma-based ambient mass spectrometry sources, including the commercially available Direct Analysis in Real Time (DART). The DART desorption/ionization source utilizes a direct-current (DC) discharge, similar to FAPA, but operates at higher helium gas flow rates (2-5 L/min), higher voltages (1,000-4,000 V), and lower currents (ca. 0.5-5 mA) than the FAPA. Additionally, the DART source incorporates auxiliary grid electrodes, to filter ions produced within the discharge, and a gas heater, to heat the gas emanating from the source and enabling thermal desorption of molecules from surfaces. The result is a discharge that is structurally and chemically different from the FAPA, but can produce similar reagent ions and, as such, molecular ions from samples.

In some embodiments, the DART source is used in place of FAPA for the described methods and assembly by placing the surface of a suspected counterfeit electronic within the heated gas stream exiting the DART source resulting in thermal volatilization of species on the surface of the chip and ionization via chemical-ionization mechanisms similar to the FAPA source. The resulting complex spectra are then processed with the same chemometric techniques (PCA and the BEAST algorithm) described herein.

It is to be understood that while DART and LTP are contemplated as ionization methods of the present disclosure, FAPA may suffer from fewer matrix effects than a DART or LTP source and may suffer from relatively few oxidation peaks, and, therefore, generate simpler spectra. The FAPA source should impart more thermal energy to the sample surface for desorption and subsequent ionization than other devices and methods such as DESI, LTP, or DART. This latter factor may be useful in obtaining useful levels of ions from the relatively 'tough', i.e., thermally stable, epoxy systems utilized for encapsulating electronic components.

Polymeric systems such as the epoxy IC encapsulants explored in this disclosure, may result in complex, congested mass spectra. Because it is desirable to compare spectra from suspected counterfeit electronics with spectra from valid, verifiable production epoxy coatings in an efficient manner for the purpose of "screening" out counterfeits, it is desirable to make use of statistical approaches, i.e., chemometrics, for analyzing and characterizing the spectra. The use of chemometrics also largely removes the element of subjective judgment from interpretation of the mass spectral "fingerprints."

Once a fingerprint mass spectrum is generated, it is compared to known standards through a chemometric approach, such as a multivariate statistical technique that returns a probability that the chip being analyzed is counterfeit. One example of a multivariate statistical technique is Principal Component Analysis (PCA), as described in Warwick & York: US, 1933, vol. 24, pp 417-441; incorporated by reference herein in its entirety. PCA was used to show overall statistical grouping of spectral data obtained as described herein. PCA reduces the dimensionality of data by projecting all points into a new data coordinate system that accounts for the greatest variance among all the data. In addition to using principal component analysis to show general grouping, the Boot-strapped Error-Adjusted Single-sample Technique or BEAST, as described herein and in R. A. Lodder and G. M. Hieftje, Appl. Spectrosc., 1988, 42, 1351-1365 and R. A. Lodder and G. M. Hieftje, Appl. Spectrosc., 1988, 42, 1500-1512; both of which are incorporated by reference herein in their entiry; is used. In some embodiments, PCA, the BEAST, or a combination of both methods is used to process mass spectral data or near infrared spectral data. Thus, the present disclosure describes coupling of ambient mass spectrometry with powerful statistical tools for rapid determination of a likelihood that electronics being analyzed are counterfeit.

In some embodiments, the BEAST is employed to compare mass spectrometric data obtained from counterfeit ICs and known standards. The BEAST algorithm is similar to the Mahalanobis metric, except the error adjustment allows for asymmetric training sets, and nothing need be assumed about the distribution of data points within an n-dimensional space. Collapsing the n-dimensional space into a univariate distribution allows parametric statistics such as the standard deviation to be utilized. These parametric statistics are helpful in obtaining directly quantifiable information without the additional grouping calculations from PCA. Additionally, as BEAST is a single-sample technique, there is no concern about the PCA space being altered as more samples are added and the variance changes.

Advantages of the methods and assembly described herein over the current state of the art include reduced analysis times, limiting the requirement for a skilled operator, and an indication of the statistical confidence of whether a chip is counterfeit or not. In some embodiments, reduction in analysis times is a result of the FAPA source functioning without sample pretreatment. A skilled operator or technician may operate that equipment, but does not make decisions about whether a chip is genuine, which removes human bias from the analysis. Chemometrics also provide a more general and flexible approach to identifying counterfeit electronic components than identifying spectral peaks that might be indicative of a genuine or counterfeit part. The method of counterfeiting could change, and previously identified peaks for genuine or counterfeit ICs could be rendered ineffective. The Examples described herein demonstrate the efficacy of using ADI-MS coupled with chemometrics to identify blacktopped counterfeit ICs. The Examples described herein also demonstrate the sensitivity of the BEAST for discrimination between genuine and counterfeit electronic parts.

Example 1

FAPA-MS Instrumentation

A pin-to-capillary geometry FAPA source, as described in J. T. Shelley, J. S. Wiley and G. M. Hieftje, Anal. Chem., 2011, 83, 5741-5748; incorporated by reference herein in its entirety; was used in Examples employing a FAPA source. As generally shown in FIG. 1, the electrode pin 13 was an arrowhead-shaped cathode to which power was supplied and the FAPA exit capillary 15 consisted of an 18 mm-long stainless-steel capillary (2.0 mm O.D., 1.3 mm I.D.). The electrode pin was positioned approximately 7 mm from the FAPA exit capillary 15. Ultra-high purity helium (Airgas Mid America, Bowling Green, Ky.) was used for all Examples, regulated by a mass flow controller (MKS instruments, Andover, Mass.) at a flow rate of 0.80 L/min, and the power supply 17 was a glow-discharge supply (Model PTV3N200X, Spellman High Voltage, Hauppauge, N.Y.) operated typically at 500 V and current-limited to 25 mA. The FAPA exit capillary 15 was held at 88 V by means of an additional power supply (Model E3612, Agilent Corporation, Santa Clara, Calif.).

Mass spectra were obtained on the analyzer 22, which was a time-of-flight mass spectrometer (HT Unique®, LECO Corporation, St. Joseph, Mich.) with minor modifications that have been detailed hereinbelow and in J. T. Shelley and G. M. Hieftje, Analyst, 2010, 135, 682-687; incorporated by reference herein in its entirety. A capillary inlet (250 mm I.D.) led to the first vacuum stage, to which a turbomolecular pump (Varian TV-81m, Varian Inc., Palo Alto, Calif.) backed by a roughing pump (Edwards 30, Edwards Vacuum, Sanborn, N.Y.) was added to improve the ability of the MS system to handle a heavy helium load. This turbo pump was backed by an additional roughing pump (TriVac D16A, Oerlikon Leybold Vacuum, Cologne, Germany). Samples were mounted on a two dimensional motorized stage (Model 12-5367-15, Semprex Corporation, Campbell, Calif.) to improve sample-location fidelity. The FAPA source was angled at 45° with respect to the horizontal for a compromise between spatial resolution and signal level, based on investigations into surface analysis in K. P. Pfeuffer, J. T. Shelley, S. J. Ray and G. M. Hieftje, J. Anal. At. Spectrom., 2013, 28, 379-387; and K. Pfeuffer, S. Ray and G. Hieftje, J. Am. Soc. Mass Spectrom., 2014, 25, 800-808; both of which are incorporated by reference herein in their entirety. Cleaned glass slides were utilized as blanks for background. Background-subtracted spectra were then processed by several alternative chemometric techniques.

Example 2

Integrated Circuit Workup

Counterfeit ICs were obtained from NSWC Crane and certified by SMT corporation (Sandy Hook, Conn.). The counterfeit components had been previously determined to be black-topped primarily by using the customary but time-consuming appearance and microscopic observational techniques. Encapsulant standards were obtained from manufacturers of non-functional IC testing and training components (Practical Components, Los Alamitos, Calif.; and Topline Corporation, Milledgeville, Ga.); the chosen standards were those that utilized encapsulation epoxies that were traceable to the epoxy manufacturer and product number. It is noted that these standards all likely use the same Novolac phenolic epoxies utilized throughout the IC industry for encapsulation. Thus, the standards were prepared with the same material, surface printing (typically by laser etching), and form factor as valid ICs, but did not contain the internal electronic circuitry. In the present disclosure, these components are referred to as "standards", "standard encapsulants" or "valid samples". Where indicated, integrated circuits were treated with a solvent system (Dynasolve 750, Dynaloy, Indianapolis, Ind.) to remove the blacktop material. Where indicated, a carefully cleaned diamond-abrasive wheel was used to physically remove the blacktopping. In both cases, the removal-processing was continued until the verified "disappearance" of the counterfeit overmarking, and/or appearance of residual "troughs" from original laser marking, by low-powered optical microscopic examination. This involved the removal of 20 to 90 μm of material, as determined by thickness measurements. Letter designations were assigned to all components used in this study to preserve the anonymity of confirmed counterfeit integrated circuits. A breakdown of all letter assignments is given in Table 1 and is summarized herein. Three types of encapsulant standards (denoted A, B and C) were used, with a lowercase s following for standard. Counterfeits (D, E and F) were analyzed, with different surface treatments denoted by the lowercase second letters: an i for intact, r for chemically removed and d for diamond-abraded.

TABLE 1

IC types with abbreviations, number of ICs and BEAST results in standard deviations

| Integrated circuit (IC) type (abbreviation) | Number of ICs | Standard deviations (average) |
| --- | --- | --- |
| Standard A | 6 | 3.0 |
| Standard B | 6 | 2.6 |
| Standard C | 12 | 2.0 |
| IC: D intact (Di) | 20 | 170 |
| IC: D chemical treated (Dr) | 20 | 521 |
| IC: D diamond treated (Drd) | 8 | 11 |
| IC: E intact (Ei) | 16 | 430 |
| IC: E chemical treated (Er) | 16 | 184 |
| IC: E diamond treated (Erd) | 9 | 11 |
| IC: F intact (Fi) | 20 | 92 |
| IC: F chemical treated (Fr) | 19 | 49 |
| IC: F diamond treated (Frd) | 9 | 3.9 |

Example 3

Data Processing

A custom-written LabVIEW® (LabVIEW 2009, National Instruments, Austin, Tex.) program was used to format the mass spectrometry data for subsequent processing by MATLAB (R2012a, MathWorks®, Natick, Mass.). The processing included removing all points below m/z 50. The entire remaining mass spectrum from 50-500 amu was used in all subsequent chemometric evaluations. The princomp feature of MATLAB was used for all PCA analysis. Formatting of the mass spectrometry data for PCA included creating a two-dimensional array containing all ICs and mass-to-charge values and subsequently transposing the data for processing within MATLAB. The BEAST algorithm was also used as described. First, the data were "bootstrapped", which involved sampling with replacement to increase the apparent size of a training set. This bootstrapped training set, in this case the standards (authentic chips), was next projected into n-dimensional space (where n was the number of data points). Then, a new, suspect sample was projected into this same space and a hypercylinder was created between this new sample point and the center of the training set. The radius of this hypercylinder was adjusted to ensure that a statistically significant number of training-set samples appeared inside the cylinder. All points within the cylinder were then collapsed into a univariate distribution by projection onto the hyperline, so conventional statistics could be utilized. Based on the distribution of training-set samples along the hyperline, a standard deviation was generated and consequently a distance, in standard deviations, by which the new, suspect sample differed from the training samples. The standard deviation permitted a statistical confidence level to be assigned to each chip. Error-adjustment refers to a comparison between the mean and the mode of the bootstrapped samples to determine if there was significant skew (defined by confidence intervals) in the training set. If the skew was significant, more bootstrap repetitions were performed to reduce the skew.

Example 4

Mass Spectra of ICs

Figure 2A:
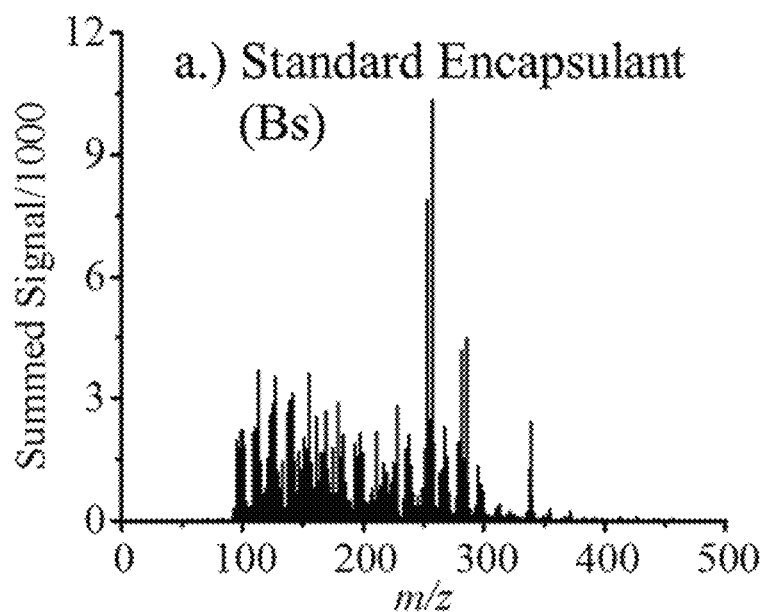
FIG. 2a is a mass spectrum generated from a genuine standard using the apparatus illustrated in FIG. 1.
Figure 2B:
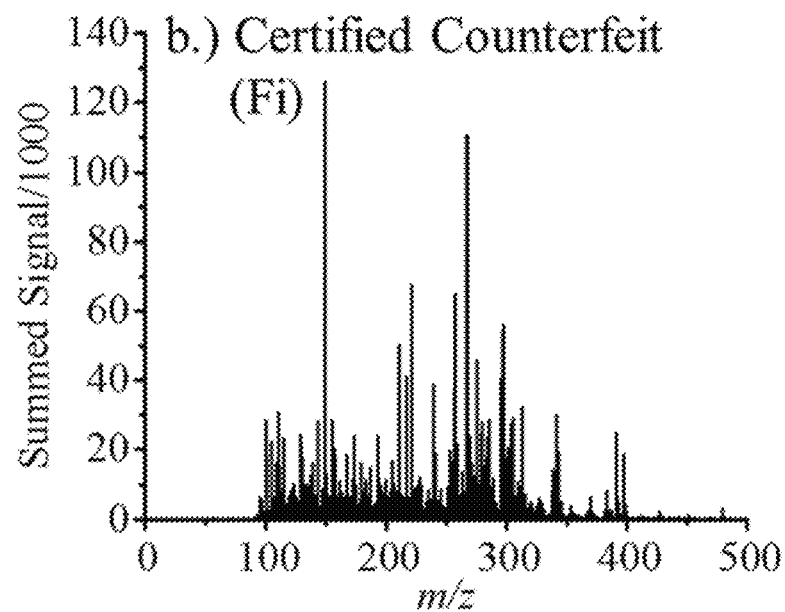
FIG. 2b is a mass spectrum generated from a certified counterfeit using the apparatus illustrated in FIG. 1.

Using the instrumentation of Example 1, ICs from Example 2, and the data processing methods described in Example 3, each IC sample was exposed to the FAPA afterglow for 60 seconds, of which spectra were integrated for the middle 30 seconds. The resulting spectra were background-subtracted, with a cleaned microscope slide being used as a blank. Example spectra from a standard (Bs) and an intact counterfeit IC (Fi) are displayed in FIGS. 2a and b, respectively. The mass spectra illustrated in FIGS. 2a and b demonstrate the complexity of the sample, and the inherent difficulties in reproducibly distinguishing between genuine and counterfeit components. Some cosmetic differences are apparent between the spectra in terms of the most abundant species, but the spectra are very congested. Rather than attempting to determine which species or peaks might be indicative of a genuine or counterfeit part, several chemometric approaches were utilized. The mass range examined was from 50-500 m/z and mass spectra were not normalized to incorporate changes in intensity into the chemometric separation.

Example 5

Classification by Principal Component Analysis without Surface Removal

Figure 3A:
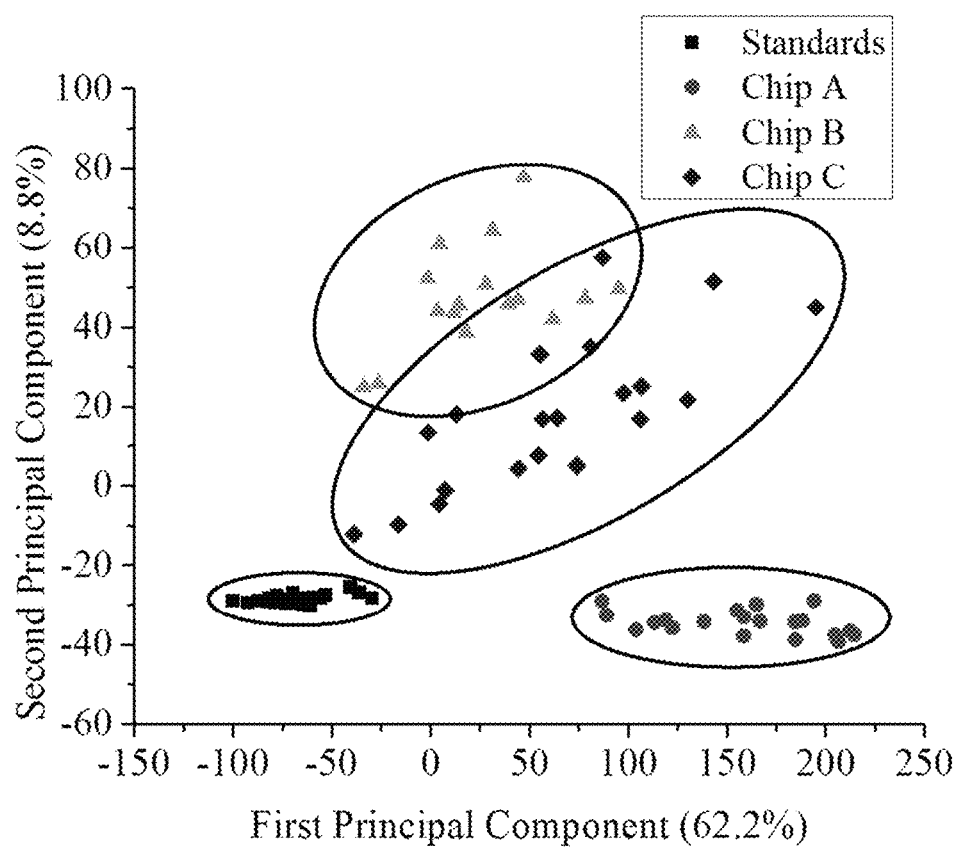
FIG. 3a is a plot of the first two principal components for three types of genuine standards and three types of counterfeit integrated circuits where percentages given in the axis labels refer to the amount of variance for which each principal component accounts.
Figure 3B:
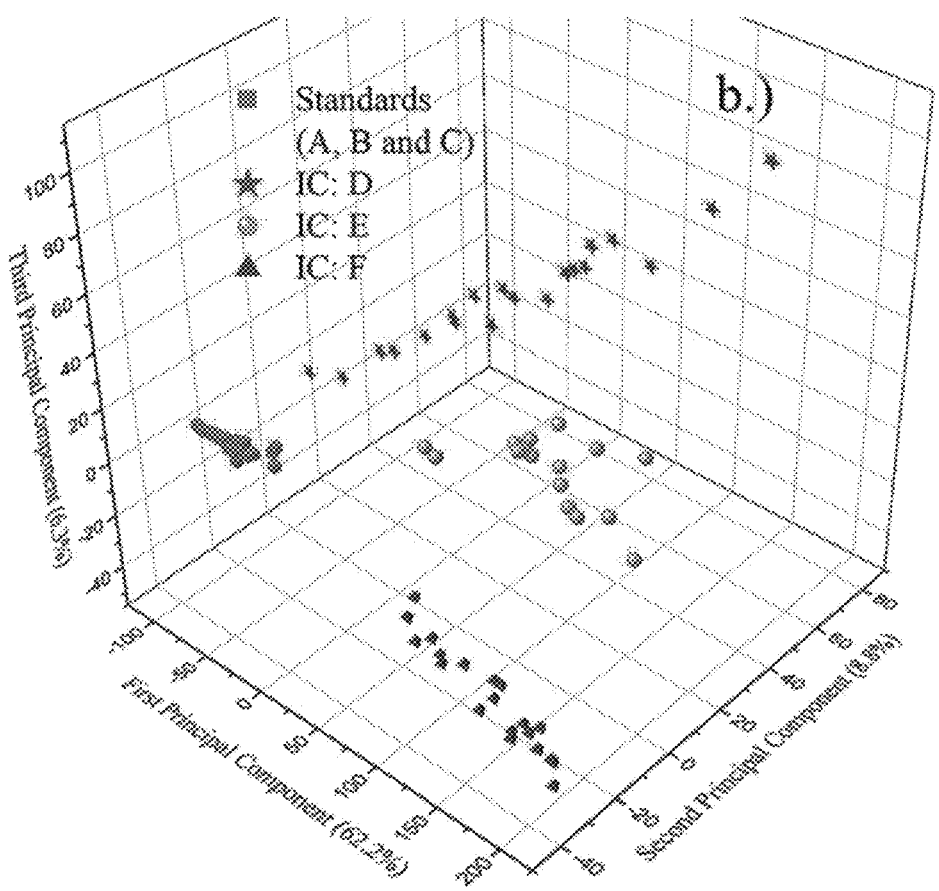
FIG. 3b is a plot of the first three principal components for three types of genuine standards and three types of counterfeit integrated circuits where percentages given in the axis labels refer to the amount of variance for which each principal component accounts.

Mass spectrometry results were first analyzed by principal component analysis to obtain a general classification of the different IC types. Three different standard encapsulants and counterfeit ICs were analyzed with PCA. A plot of the first two principal components for the 24 genuine chips (A, B, and C) and 56 counterfeit chips (D, E, and F) is illustrated in FIG. 3a. Percentages given in the axis labels refer to the amount of variance for which each principal component accounts. In total, 71% of the variance present among all spectra is represented in FIG. 3a. Only three main groups were differentiated, and correspond to a group for counterfeit ICs D and E, a group for counterfeit IC F, and one for the standards (A, B and C). Circles were added to show the overall groupings. Counterfeit integrated circuits D and E were not grouped far enough apart to be considered separated by PCA. Despite coming from two different manufacturers, the three encapsulant standards (A, B and C) formed a small group. This tight grouping was both evidence of strict manufacturing tolerances and the fact that the various valid encapsulant materials used as standards were all based on similar Novolac-based epoxies. The three counterfeit ICs also grouped away from the standards. The group for counterfeit IC F was spaced well away from that for the standard materials, whereas ICs D and E formed an overlapping group. These results reveal that significant differences in variance within the mass spectral fingerprint exist between the standard materials and the counterfeits. Additionally, the counterfeit ICs produced a much broader distribution within the PCA space than the standard materials. Both of these characteristics also can be of advantage with other chemometric techniques. Addition of the third principal component is illustrated in FIG. 3b. Addition of the third principal component successfully distinguished between the overlapping group of IC sets D and E. This separation confirmed that PCA can successfully discriminate between genuine and counterfeit chips, based on the distinct groupings illustrated, especially as dimensions are added.

Example 6

Figure 4:
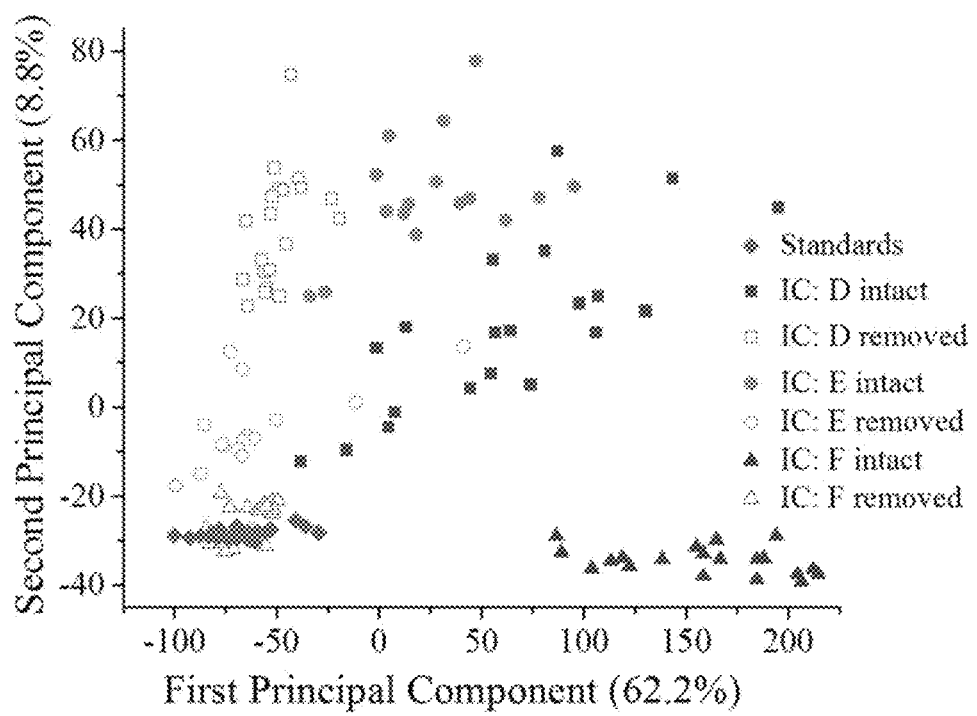
FIG. 4 is the plot of FIG. 3a with additional results for three types of counterfeit ICs for which the surface has been chemically removed.

Classification by Principal Component Analysis after Chemical Surface Removal Using the instrumentation of Example 1, ICs from Example 2, the data processing methods described in Example 3, and methods of Example 4, counterfeit ICs were treated with Dynasolve 750 solvent system to remove the suspected blacktop layer and processed again with PCA. As shown in FIG. 4, the surface treatment changed the PCA distribution of the surface-treated ICs, which are indicated by open symbols. With counterfeit IC sets D and E, either residues of the blacktop material remained after treatment, or possibly there may have been some degree of surface chemical modification of the Novolac epoxy substrate by the extended processing treatment because these components did not group with the standards but were shifted from their original locations within the PCA space. Set D grouped closer together after solvent treatment, yet farther from the set of standards. The set of counterfeit ICs E shifted toward the standards, but did not group with them, which supports that surface removal by the solvent was incomplete. Only in the case of counterfeit IC set F did a set coincide completely with the standard material. With IC set F, the blacktopped layer may have been thin enough that treatment with the solvent was sufficient to completely remove it and result in grouping well with the standards.

Example 7

Figure 5:
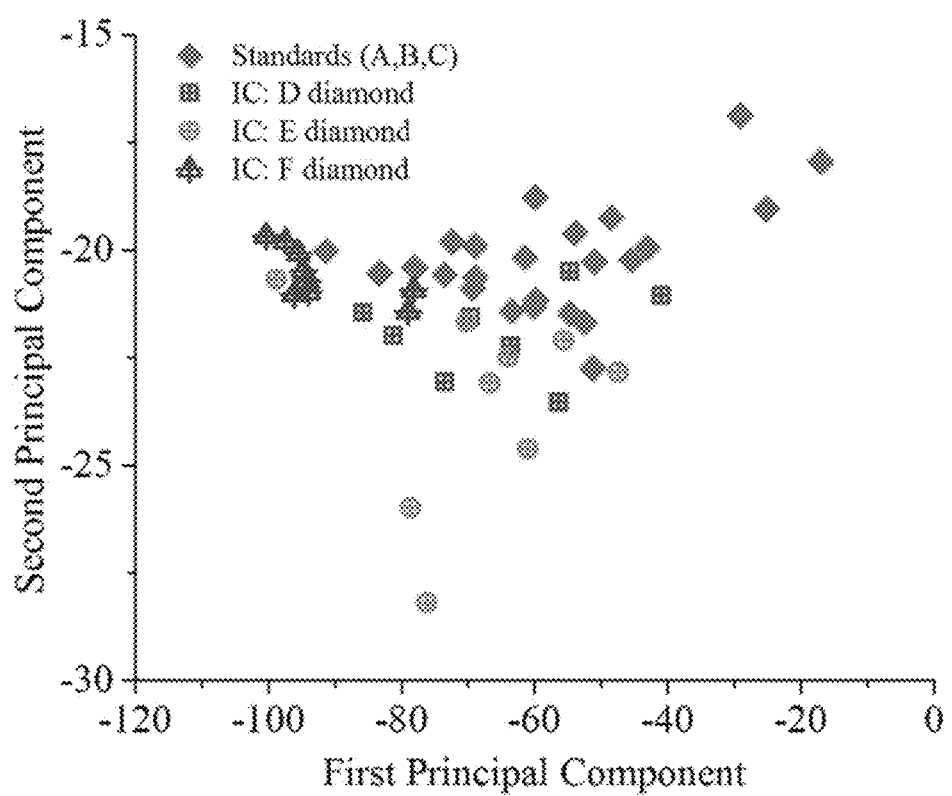
FIG. 5 is a plot of the first two principal components for three types of genuine standards and three types of counterfeit ICs for which the surface has been removed by diamond-wheel abrasion (a, b, and c) where percentages given in the axis labels refer to the amount of variance for which each principal component accounts.

Classification by Principal Component Analysis after Mechanical Surface Removal Using the instrumentation of Example 1, ICs from Example 2, the data processing methods described in Example 3, and methods of Example 4, a diamond abrasive wheel was utilized to mechanically remove a substantial portion (20-90 μm) of the surface of the ICs. A subset of the original counterfeit components (see Table 1 for numbers) underwent a surface abrasion procedure and was again classified by means of PCA. A zoomed-in view of the PCA space directly surrounding that of the standards is shown in FIG. 5. This figure illustrates how well the diamond-abraded samples (Drd, Erd and Frd, shown as cross-filled open symbols) grouped with the encapsulant standards. Because these diamond-abraded samples grouped very well with the standards in the PCA space, blacktopping was the apparent mode of counterfeiting for these ICs. This finding suggests that the blacktop layer was typically between 20 and 90 μm thick, as that was the amount of material removed from these ICs that caused them to group directly with the standards.

Example 8

BEAST Study

Figure 6A:
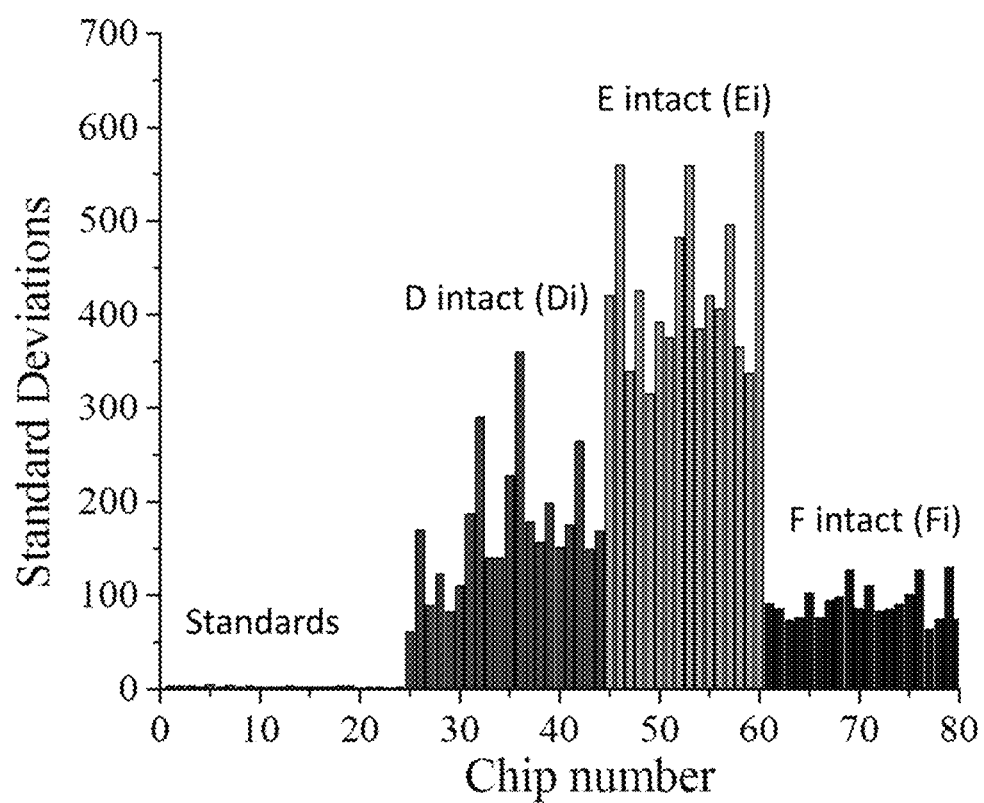
FIG. 6a is a bar-graph showing the results of BEAST analysis on three types of genuine standards and three different types of counterfeit ICs, which shows successful discrimination between standard and counterfeit components.
Figure 6B:
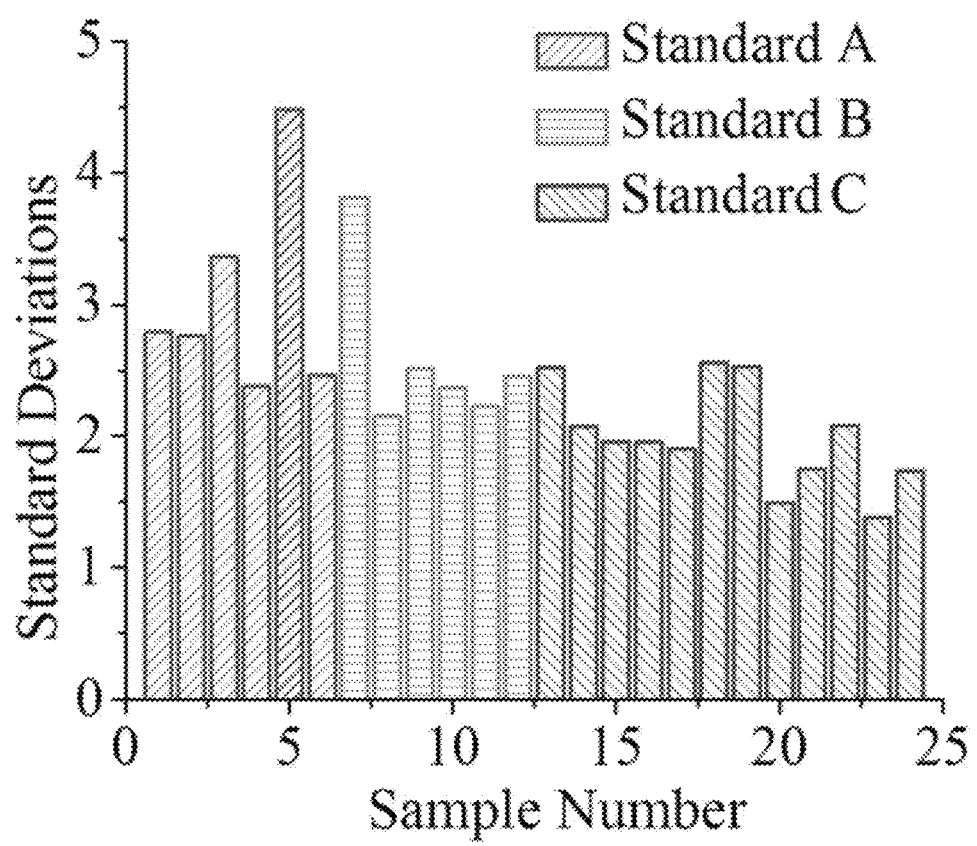
FIG. 6b is the graph of FIG. 6a zoomed in on the results of BEAST analysis on the three genuine standards, which shows the self-consistency of the algorithm.
Figure 7:
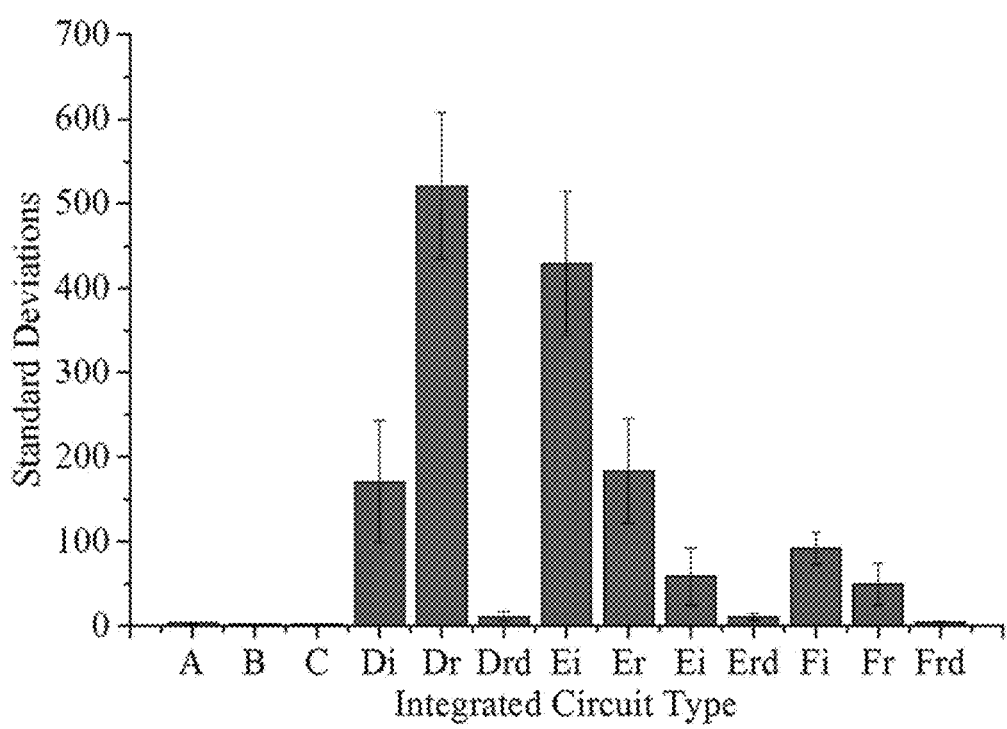
FIG. 7 is a bar-graph showing the average BEAST analysis results for three genuine standards and three different types of counterfeit ICs, where each type of counterfeit ICs includes untreated, chemically treated, and diamond-abraded counterfeit ICs.

The BEAST algorithm, a more rigorous statistical technique, was also applied to the mass spectral data of the standards, counterfeit ICs without surface modification, counterfeit ICs with chemical surface modification, and counterfeit ICs with diamond abraded surfaces. The bootstrapped error adjusted single-sample technique (BEAST) was suited for a task of quantitative estimation of whether a sample belongs to a training set (here the "universe" of valid samples) or not as it returns a number, in terms of standard deviations, that directly corresponds to how similar a new sample is to the training set. The smaller the standard deviation, the closer the sample was to the training set. The encapsulant standards were used as the training set and bootstrapped 1000 times; afterward, each of the counterfeit ICs as well as the chemically and physically surface-removed ICs were run through the BEAST algorithm; the results are shown in Table 1 and FIG. 6a. To test the self-consistency of the algorithm, the individual standards were also run (i.e. treated as new samples); the results are shown in Table 1 and FIG. 6b. All of the standards were less than 5 standard deviations away from the bootstrapped set which, similar to the PCA results, demonstrated the tight manufacturing tolerances of the standards. The individual standard deviations were averaged for each population and are displayed in FIG. 7, with error bars representing plus/minus one standard deviation. The error bars for the standards (A, B, and C) are virtually invisible compared to those of the other (counterfeit) samples. The individual standard deviations based on the BEAST results of Example 8 were averaged for each population and are displayed in FIG. 7. Population averages for each type of IC in FIG. 7 show the ability of the BEAST algorithm to distinguish counterfeit ICs. All of the certified counterfeit ICs averaged 100 or more standard deviations away from the standard set. This finding demonstrates the sensitivity of the algorithm for recognizing counterfeit ICs.

Example 9

BEAST Results after Chemical Surface Removal

If the chemical treatment removed the surface adulterant, the counterfeit chemically treated ICs should have been a relatively lower number of standard deviations away from the standard set compared to the counterfeit untreated ICs. Two of the counterfeit IC sets (E and F) displayed this behavior, while IC set D moved a greater distance from the training set. These findings agreed with the PCA results shown in Example 6 and FIG. 4 where IC set D shifted farther away from the standards in the PCA space while set E moved closer and set F coincided entirely with the standards. This inconsistency of the response of the chemical removal samples in the BEAST algorithm once again is suggestive of either residual blacktopping material after treatment or chemical modification of the original epoxy substrate, or perhaps a combination of both effects.

Example 10

BEAST Results after Mechanical Surface Removal and Verification of Blacktopping The samples that had been abraded with the cleaned diamond wheel all shifted to a low number of standard deviations from the training set, as shown in FIG. 7. Thus the fingerprints of counterfeit IC substrates for which the blacktopping had been removed by the relatively chemically clean abrasive method were very similar to the fingerprints of the standards. The large differences for the counterfeit IC surfaces from the standards plus this close match between the mass spectral results for the standards and those for which the blacktopping layer was most cleanly removed provides further validation of this methodology for anti-counterfeit screening in that it returns closely similar results for the standards and the counterfeit substrates, which all would have been originally produced from similar epoxy materials.

Table 1 lists the average standard deviation for each set of ICs, as well as the number of ICs in each category. Population averages for the diamond-wheel-treated samples showed a consistent decrease in standard deviation compared to the original counterfeit samples. This reduction in standard deviations means the ICs possess more standard-like characteristics, which supports that blacktopping was the method of counterfeiting. The diamond-treated samples Frd were within 5 standard deviations of the training set, indicating they behaved like the standards. Diamond-removed IC sets Drd and Erd were within 11 standard deviations, which is an improvement from the chemically treated sets, but not within 5 standard deviations such as the standards or set of counterfeit ICs Frd. The reason these two sets did not group exactly with the standards is either that the blacktopped layer was not completely removed through physical abrasion, or that the diamond wheel exhibited memory effects.

These Examples thus demonstrate the utility and efficacy of the described methods to identify ICs altered by blacktopping. A plasma-based source for ambient desorption/ionization mass spectrometry, the flowing atmospheric pressure afterglow (FAPA) source, in conjunction with chemometric methods, was well suited for evaluating the surface of discrete electronic components. Principal component analysis demonstrated that counterfeit electronic ICs can be differentiated successfully from standard encapsulated ICs. Surface removal through physical abrasion caused the remainder of the counterfeit samples to group with the standards within the PCA space and provided evidence that black-topping was the method of counterfeiting. The BEAST algorithm was used with mass spectrometry data to provide discrimination from a training set. Further support was found that the counterfeit ICs were made through a blacktopping procedure when the diamond-abraded counterfeit samples were fewer standard deviations away from the training set than the untreated counterfeit samples through determination with the BEAST algorithm.

What is claimed is:

1. A method for identification of a counterfeit electronic, the method comprising subjecting a suspected counterfeit electronic to an ambient desorption/ionization (ADI) source under atmospheric pressure to energize compounds at a surface of the suspected counterfeit electronic, detecting properties of the compounds at the surface, and comparing the properties of the compounds at the surface to a standard, wherein the standard and the suspected counterfeit electronic are not pretreated.

2. The method of claim 1, wherein the energy source desorbs and ionizes the compounds at the surface of the suspected counterfeit electronic.

3. The method of claim 2, wherein detecting properties of the compounds at the surface comprises generating a mass spectrum of ions resulting from the compounds at the surface.

4. The method of claim 2, wherein the energy source is flowing atmospheric pressure afterglow (FAPA).

5. The method of claim 2, wherein the energy source is direct analysis in real time (DART).

6. The method of claim 1, wherein the energy source is selected from the group consisting of ultraviolet light, visible light, near-infrared light, infrared light.

7. The method of claim 1, wherein comparing the properties of the compounds at the surface to a standard comprises using a chemometric method to process data describing the properties of the compounds at the surface.

8. The method of claim 7, wherein the chemometric method is a multivariate statistical technique.

9. The method of claim 8, wherein the multivariate statistical technique is principal component analysis (PCA).

10. The method of claim 9, wherein comparing the properties of the compounds at the surface to a standard further comprises using the bootstrapped error-adjusted single sample technique (BEAST).

11. The method of claim 7, wherein the chemometric method is the bootstrapped error-adjusted single sample technique (BEAST).

12. The method of claim 11, wherein detecting properties of the compounds at the surface comprises generating a mass spectrum of ions resulting from the compounds at the surface and the data comprise mass spectra.

13. The method of claim 1, wherein the suspected counterfeit electronic is a suspected counterfeit integrated circuit and the standard is derived from a genuine integrated circuit.

14. The method of claim 1, wherein the suspected counterfeit electronic is suspected of being altered by blacktopping.

15. A method for identification of a counterfeit electronic, the method comprising subjecting a suspected counterfeit integrated circuit to an ambient desorption/ionization (ADI) source under atmospheric pressure to ionize and desorb compounds at a surface of the suspected counterfeit electronic, generating a mass spectrum of ions resulting from the compounds at the surface, and comparing the mass spectrum to a standard using a chemometric method.

16. The method of claim 15, wherein the chemometric method is selected from the group consisting of principal component analysis (PCA), the bootstrapped error-adjusted single sample technique (BEAST), and a combination thereof.

17. An apparatus for identification of a counterfeit electronic, the apparatus comprising an ambient desorption/ionization (ADI) source to desorb and ionize compounds directly from a surface of a suspected counterfeit electronic under atmospheric pressure with no pretreatment, a mass spectrometry detector coupled to the ADI source to detect ions resulting from the surface, and at least one programmable machine programmed for comparing the ions to a standard by a chemometric method and returning a confidence that the suspected counterfeit electronic being analyzed is counterfeit.

18. The apparatus of claim 17 wherein the chemometric method is selected from the group consisting of principal component analysis (PCA) and the bootstrapped error-adjusted single sample technique (BEAST).

19. A method for identification of a counterfeit electronic, the method comprising subjecting a suspected counterfeit electronic to an ambient desorption/ionization (ADI) source under atmospheric pressure to energize compounds at a surface of the suspected counterfeit electronic, detecting properties of the compounds at the surface, and comparing the properties of the compounds at the surface to a standard, wherein the chemometric method is selected from the group consisting of principal component analysis (PCA) and the bootstrapped error-adjusted single sample technique (BEAST).

* * * * *